United States Patent [19]

Kimoto et al.

[11] Patent Number: 4,959,537
[45] Date of Patent: Sep. 25, 1990

[54] METHOD AND APPARATUS FOR INSPECTING TRANSPARENT CONTAINERS

[75] Inventors: Tetsuya Kimoto, Yawata; Masashi Nakagawa, Neyagawa, both of Japan

[73] Assignee: Matsushita Electric Works, Ltd., Japan

[21] Appl. No.: 365,934

[22] Filed: Jun. 13, 1989

[30] Foreign Application Priority Data

Jun. 16, 1988 [JP] Japan .................. 63-149000

[51] Int. Cl.⁵ ............................................. G01N 21/90
[52] U.S. Cl. .................... 250/223 B; 356/240
[58] Field of Search .................. 250/223 B; 209/524, 209/526; 356/240, 428

[56] References Cited

U.S. PATENT DOCUMENTS

| 4,256,957 | 3/1981 | Ford et al. | 250/223 B |
| 4,428,673 | 1/1984 | Yoshida | 356/240 |
| 4,448,526 | 5/1984 | Miyazawa | 250/223 B |

FOREIGN PATENT DOCUMENTS

| 2834587 | 3/1979 | Fed. Rep. of Germany . |
| 2848219 | 5/1980 | Fed. Rep. of Germany . |
| 2848316 | 5/1980 | Fed. Rep. of Germany . |
| 2909061 | 9/1980 | Fed. Rep. of Germany . |
| 3029678 | 3/1982 | Fed. Rep. of Germany . |
| 3124949 | 3/1982 | Fed. Rep. of Germany . |
| 55-144533 | 11/1980 | Japan . |
| 57-12352 | 1/1982 | Japan . |
| 57-64153 | 4/1982 | Japan . |
| 2078940 | 1/1982 | United Kingdom . |

Primary Examiner—Edward P. Westin
Attorney, Agent, or Firm—Stevens, Davis, Miller & Mosher

[57] ABSTRACT

A method and apparatus for inspecting a transparent container having a defect on the container bottom by monitoring and analyzing the light energy transmitted through the container bottom. A source of diffused illumination is provided to direct the diffused illumination through the container bottom for monitoring the light energy by camera. The diffused illumination is arranged to be directed in intensity greater through a peripheral region than through a central region of the container bottom so as to positively produce a pair of peak values in light energy distribution received by the camera along at least one dimension corresponding to a line or secant extending in a plane of the container bottom. A corresponding pair of positions having such peak values and spaced along the dimension is obtained as indicative of the opposed peripheral edges of the container bottom, which positions are then processed to provide a true center of the monitored image as corresponding to the center of the container bottom. Based upon thus determined center of the image, it is defined an inspection zone which is in exact coincidence with the actual container bottom and within the confines of which the monitored light energy is analyzed to detect a defect on the container bottom. Thus, the defect inspection can be made free from an erroneous background outside of the container bottom to give a reliable detection of a defect on the container bottom.

20 Claims, 10 Drawing Sheets

METHOD AND APPARATUS FOR INSPECTING TRANSPARENT CONTAINERS

BACKGROUND OF THE INVENTION

1. Field of the Invention

The present invention is directed to a method and apparatus for inspecting a transparent container, having a defect on the container bottom, and more particularly to a method and apparatus for such inspection in which a zone of inspection is optically determined in exact coincidence with the container bottom for reliable inspection free from a background error.

2. Description of the Prior Art

It is known in the art to utilize optical scanning technique for detection of a defect or contamination on the bottom of a transparent container such as a beer bottle, in which a diffused illumination is directed through the container bottom to monitor and analyze a variation in the light energy transmitted through the container bottom and detect a defect or contamination when a critical variation in the light energy is found.

The above inspection technique has a problem when utilized in a feed line, i.e., washing line or the like container processing line for successively inspecting the containers moving at a high speed along the line. The problem encountered is the difficulty in obtaining an exact registration of the monitored field of view with the actual container bottom ever moving through an inspection station. Such misregistration will eventually lead to an erroneous inspection result since the system cannot recognize the exact image of the container bottom rather images in processed with regard to an unintended portion outside of the container bottom. For example, when such misregistration occurs, the system may recognize the image of the portion outside of the container bottom as indicative of a defect within the container bottom, resulting in a false detection. This problem becomes more and more critical, particularly when the inspection is required for the containers moving fast the processing line.

Figure 15A:
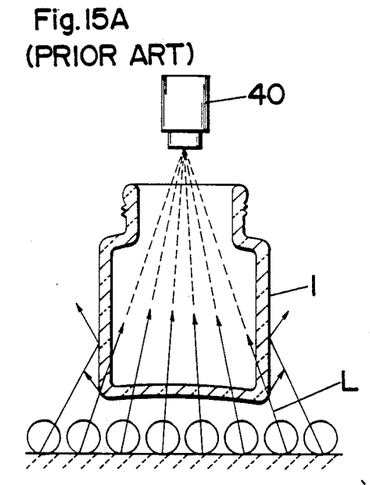
FIGS. 15A, 15B, 16A, and 16B are diagrams explaining the background of the present invention.
Figure 15B:
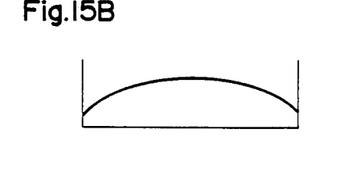
Figure 16A:
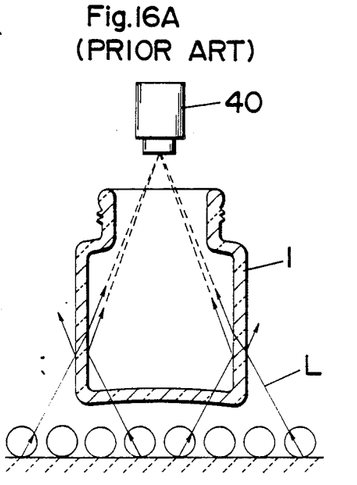
Figure 16B:
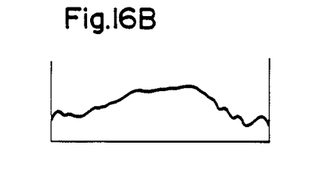

Consequently, there is an serious need to define an exact inspection zone in correspondence to the actual container bottom so that the optical analysis can be correctly limited to optical information only within the actual container bottom and without being confused by erroneous information coming from the outside of the container bottom. However, with the known optical inspection systems, such as disclosed in Japanese Patent Publication (KOKAI) No. 57-12352, it is difficult or substantially impossible to define an inspection zone in exact coincidence with the actual container bottom. The reason can be discussed with reference to FIGS. 15 and 16 which schematically illustrate the conventional container bottom inspection system in which diffused illumination L is directed through the bottom of a container 1 to be monitoring by a camera 40 positioned upwardly of the container 1. In the conventional system, the diffused illumination is selected to be uniform in intensity across the container bottom. Thus, as illustrated in FIG. 15A, the light directed to the peripheral edge of the container bottom is considerably deflected thereat and also the light directed to the sidewall of the container is reflected thereat because of its small angle of incidence, so that there is seen a considerable reduction in the light energy passing through the peripheral region of the container bottom and the portion outside thereof in relation to the light energy passing through the central region of the container bottom [as shown in FIG. 15B]. Although such light energy reduction at the portion outside of the periphery of the container bottom is thought to be well indicative of the boundary of the container bottom and could be utilized to define the actual zone of inspection in correspondence with the container bottom, such energy reduction will not actually occur because of an internal reflection of light within the container 1, as seen in FIG. 16A. That is, the light after passing the container bottom and after being directed to the inner surface of the container sidewall is reflected thereat to be redirected toward the camera 40 as if it comes through the peripheral region or the sidewall outside of the container bottom. Since the camera 40 cannot discriminate such reflected light from the non-reflected light, the internally reflected light acts to add the light energy which the camera 40 recognizes as coming from other than the central region of the container bottom. With this result, the camera 40 provides the resulting light energy intensity distribution of FIG. 16B in which no clear optical characteristic is seen for indicative of the boundary of the container bottom, failing to define an inspection zone in exact coincidence with the actual container bottom.

SUMMARY OF THE INVENTION

The above-mentioned problem can be eliminated by the present invention which proposes a unique and novel technique for defining an exact inspection zone in exact coincidence with the container bottom for reliable inspection thereof. In the present invention, a container is positioned upright with its bottom adjacent a source of diffused illumination to be inspected by the use of a camera disposed above the container. The source of diffused illumination is directed through the container bottom in such a manner that the diffused illumination is greater in intensity at a peripheral region than at a central region of the container bottom. The light energy transmitted through the container bottom is monitored to provide a distribution pattern of the light energy along at least one dimension corresponding to a line or band extending in the plane of the container bottom. Due to the greater illumination level at the peripheral region than at the central region, the distribution pattern is found to have a pair of peak values at spaced positions along the dimension respectively as corresponding to the peripheral edges of the container bottom. From such discriminative positions, it is calculated a midpoint thereof which is then processed to provide a center point for the container bottom. The center point is then utilized to define an inspection zone in an exact registration with the actual container bottom within the confines of which the light energy and is analyzed for detection of a defect on the container bottom.

Accordingly, the analysis of the light energy transmitted through the container can be effected for only and entire zone of the true container bottom for reliable detection of a defect on the bottom without being interfered by the illumination coming through portions or an unintended zone other than the container bottom.

Such inspection technique can be easily adapted without requiring a special scheme to an inspection system for containers which are moving fast in a continuous processing line. Also with the use of the diffused illumination which is greater in intensity at the peripheral region of the container bottom, it is possible to enhance detection of defects on the peripheral region which would be otherwise short of illumination level due to an unnegligible amount of reflection possibly developed thereat by the presence of a crack or the like minor failure.

It is therefore a primary object of the present invention to provide a method and apparatus which is capable of defining an inspection zone in exact registration with the container bottom for reliable inspection with the enhanced detection of defects at the peripheral region of the container bottom.

In preferred embodiments, the light energy distribution is monitored with respect to each of first and second dimensions which are selected to extend in the inspection field of view in corresponding relation to two lines extending perpendicular to each other in the plane of the container bottom. Then, it is obtained from the respective light energy distributions first and second midpoints between a pair of spaced positions having peak values of the monitored light energy. It is from thus obtained first and second midpoints that the true center of the container bottom is determined as an intersection between the perpendicular bisectors passing through the first and second midpoints, respectively.

The source of the diffused illumination is arranged in generally parallel relation to the container bottom so that the most of the light directed to the container sidewall is reflected thereat due to less angle of incidence to thereby considerably reduce the light energy transmitted through the container sidewall and reaching the camera. With this result, monitored light energy distribution shows a remarkable drop at the portions corresponding to the peripheral edges of the container bottom to thereby positively present the peak values of the light energy in cooperation with the above-mentioned arrangement of directing the diffused illumination which is greater in intensity at the peripheral region than at central region of the container bottom.

For providing a greater intensity of diffused illumination at the peripheral region than at the central region of container bottom, the present invention proposes in one embodiment to utilize a pair of first and second diffuser plates arranged between a lamp source and the container bottom. The first diffuser plate has a diffusing surface which covers the entire container bottom, while the second diffuser plate has a smaller area of diffusing surface than the first diffuser plate such that the light directed toward the central region of the container bottom is twice diffused or attenuated through the first and second diffuser plates while the light directed toward the peripheral region in only once diffused or attenuated, whereby illuminating the peripheral region of the container bottom to a greater intensity than the central region. Alternatively, a single diffuser plate which has a thickness which is greater at a central portion than at a peripheral portion may be utilized so as to attenuate the illumination passing through the central portion of the diffuser plate to a greater extent than through the peripheral portion of the diffuser plate.

In another version, the source of diffused illumination is arranged to have a plurality of lamp sources and a diffuser plate of uniform thickness disposed between said lamp sources and the container bottom. The lamp sources are disposed in a greater distribution density at a peripheral portion corresponding to the peripheral region of the container bottom than at a central portion so as to provide the greater illumination level at the peripheral region of the container bottom.

In a further version of the present invention, the source of diffused illumination includes convergent lenses in addition to a lamp source and a diffuser plate of uniform thickness. The lenses act to converge the rays of light from the lamp source through the diffuser plate in such a way as to develop an additional amount of the diffused illumination which is directed or oriented through the peripheral region of the container bottom toward the camera.

In a further version, the source of diffused illumination is arranged to have a first lamp source disposed in coincidence with the central portion of the container bottom, a second lamp source disposed in adjacent relation to the periphery of the container bottom, and a diffuser plate positioned to direct the diffused illumination the first and second lamp sources to the container bottom. The second lamp source is disposed to be closer to the container bottom than the first lamp source to intensify the diffused illumination directed through the periphery of the container bottom.

In a further version of the present invention, the source of diffused illumination includes, in addition to a lamp source and a diffuser plate, a reflector which redirects the light from the lamp source toward the container bottom. The diffuser plate is positioned and limited to provide the diffused illumination which is directed through the central region of the container bottom to the a monitoring spot or camera with the light energy of the lamp source being partially absorbed by the diffuser plate. The reflector is arranged to have a diffuser surface reflecting the light form the lamp source in a direction of directing the diffused illumination through the peripheral region of the container bottom toward the monitoring spot or camera without passing through the diffuser plate Thus, the diffused illumination directed through the peripheral region is not attenuated by the diffuser plate to thereby provide a greater intensity of illumination at the peripheral region than at the central region of the container bottom.

The present invention discloses a still further advantageous and unique technique to effectively discriminate the light transmitted through the container bottom from that not transmitted therethrough. For this purpose, an interference filter is utilized to pass only a particular band of wavelength which corresponds to that of the light after passing through the container, whereby excluding the other wavelength originated directly from the lamp source or an environmental light source. The interference filter is also known to have a characteristic of remarkably lowering transmissivity with respect to the light of particular band of wavelength when the light arrives the filter at an angle of incidence exceeding a critical angle. By utilizing this characteristics to the interference filter and suitably selecting the distance between the interference filter and the container bottom, the interference filter can pass only the light transmitted through the container bottom as having an angle of incidence less than the critical angle, while substantially excluding the light transmitted from outside of the bottom as having an angle of incidence more than the critical value.

It is therefore an object of the present invention to provide a method and apparatus which can successfully discriminate the light transmitted only through the container bottom or the target inspection area from the outside light for reliable definition of the inspection zone on the monitored field of view and enhancement of defect inspection.

In an apparatus of the present invention, reject means is included to reject a container in which a defect is found within the inspection zone so that the apparatus can be well adapted in a washing or the like process lines in which the containers are successively inspected and should be rejected from that line when a defect is found, which is therefore a further object of the present invention.

These and other objects and advantageous features of the present invention will become apparent from the following description of the preferred embodiments when taken in conjunction with the attached drawings.

DETAILED DESCRIPTION OF THE PREFERRED EMBODIMENTS

First embodiment <FIGS. 1 to 7>

Referring to FIGS. 1 to 7, there is shown an inspection system for transparent containers in accordance with a first embodiment of the present invention.

Figure 1:
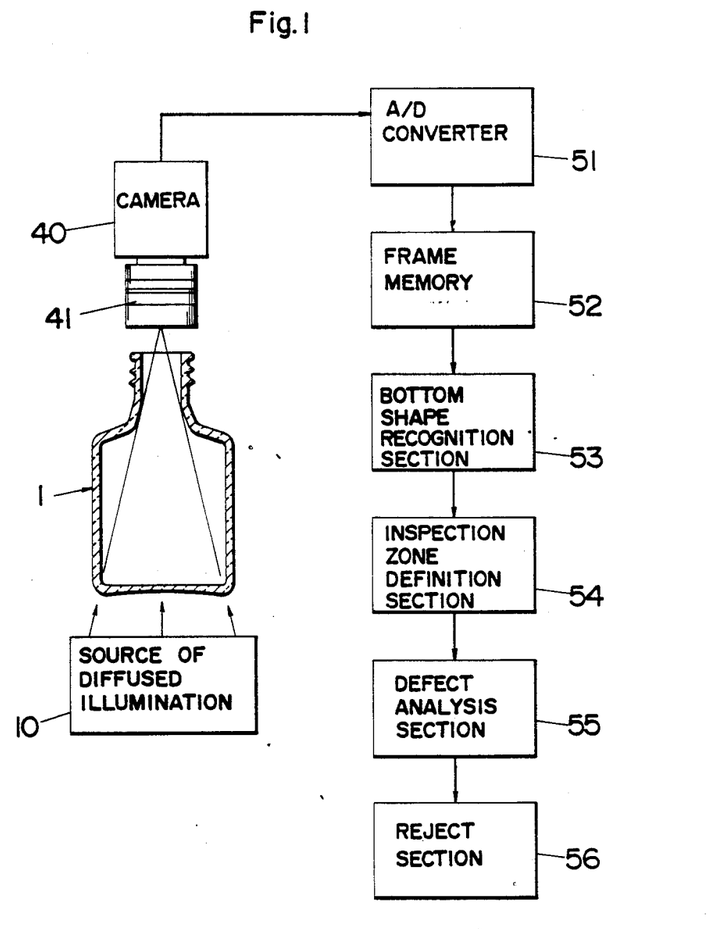
FIG. 1 is a schematic illustration of an inspection system of the present invention.

FIG. 1 illustrates a schematic diagram of an inspection unit of the system which comprises a source 20 of diffused illumination for directing the diffused illumination to the bottom of a container 1, a camera 40 monitoring the light transmitted through the container 1, and several processing sections for inspection of a defect on the container bottom.

Figure 2:
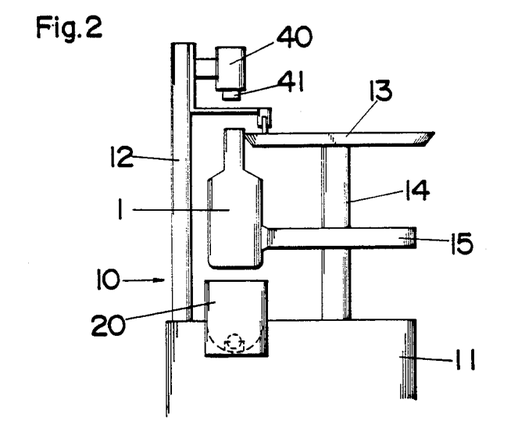
FIG. 2 is an elevation schematically illustrating an inspection station in the system.
Figure 3:
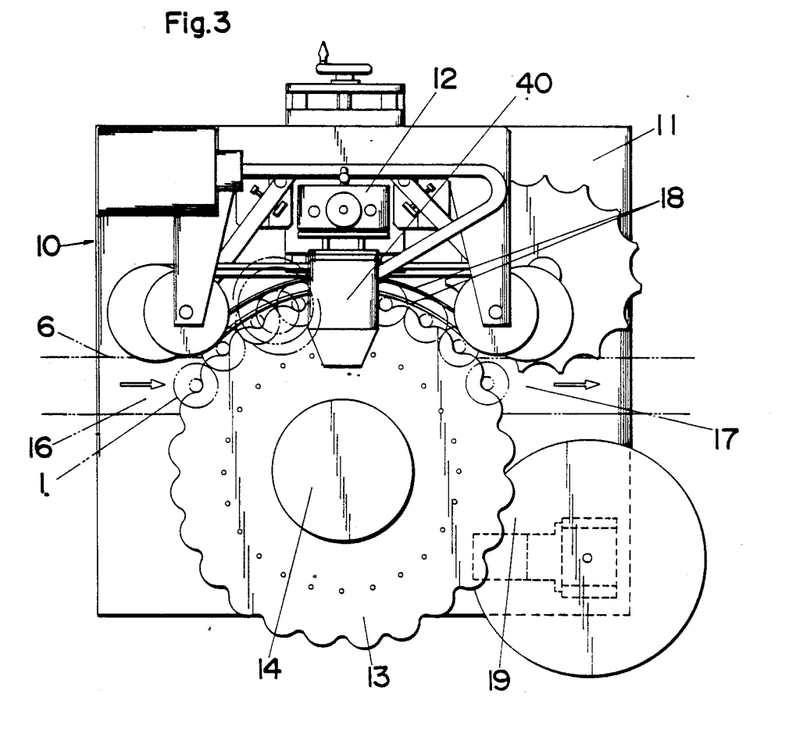
FIG. 3 is a plan view of the inspection station.
Figure 4:
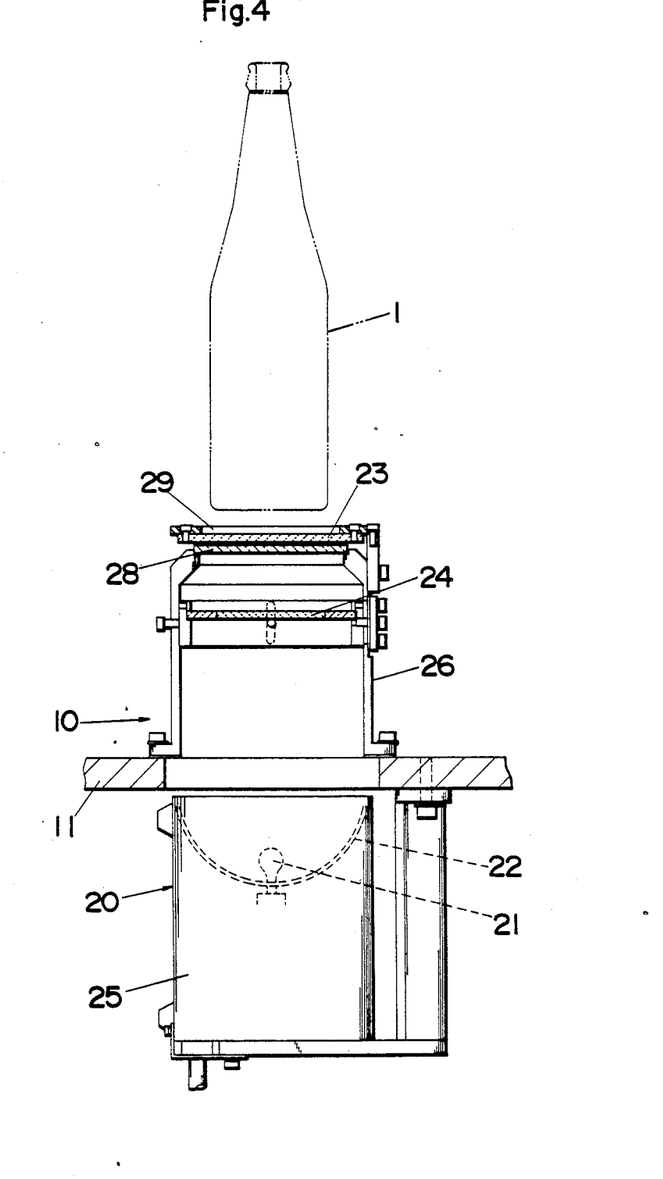
FIG. 4 is an elevation illustrating a transparent container inspection apparatus in accordance with a first embodiment of the present invention.

The inspection unit is incorporated in a processing line such as a container washing line to detect an unacceptable defect on the container bottom and reject the container 1 having such defect from the line. The container 1 to be inspected is a transparent or semi-transparent container, for example, a beer bottle with a circular bottom configuration. As shown in FIGS. 2, 3, and 4, the system includes an inspection station 10 through which containers 1 are successively passed for inspection of a defect on the container bottom. The inspection station 10 comprises a base 11 mounting the source 20 of diffused illumination and the camera 40 at the upper end of a post 12. A starwheel 13 is mounted on the base 10 to rotate about an upright drive axle 14 to catch the containers 1 by the upper ends or the mouths thereof while successively feeding the containers 1 one by one past the station 10 That is, as shown in FIG. 3, the starwheel 13 receives the containers 1 from a conveyor line 6 at an entrance 16 so as to feed them past the station 10 and back to the conveyor line 6 at an exit 17 as it rotates in the clockwise direction in the figure. A pair of belts 18 are provided in the station 10 to support the containers 1 at their sides opposite from the starwheel 13. Cooperative with the starwheel 13 is a suction rod 15 which holds the container i at the lower side portion by a suction force so as to bring the container in a correct position between the source 20 of the diffused illumination and the camera 40. When no defect is found at the station 10, the containers 1 are transported by the starwheel 13 to the exit 17 where the suction rod 15 release the container 1, after which it is fed back to the conveyor line 6. On the other hand, when an unacceptable defect is found, the container 1 is transported by the starwheel 13 through an extended angular displacement to a reject exit 19 where it is released by the suction rod 15 and recovered as a rejected container.

Figure 5:
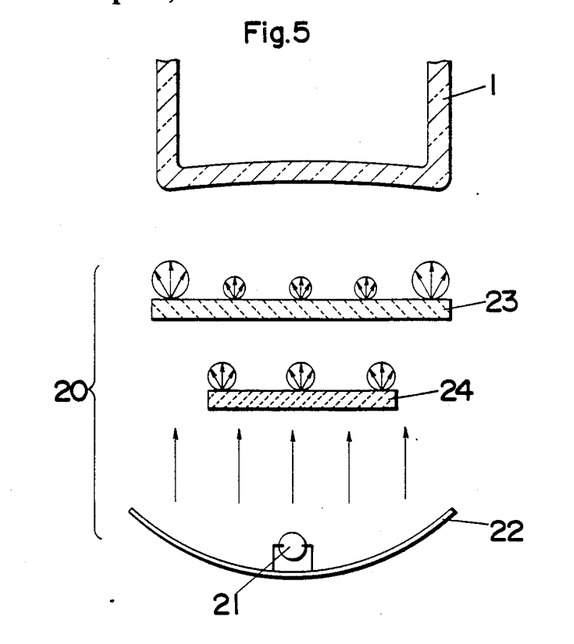
FIG. 5 is a schematic illustration of a source of diffused illumination utilized in the first embodiment of the apparatus.
Figure 17:
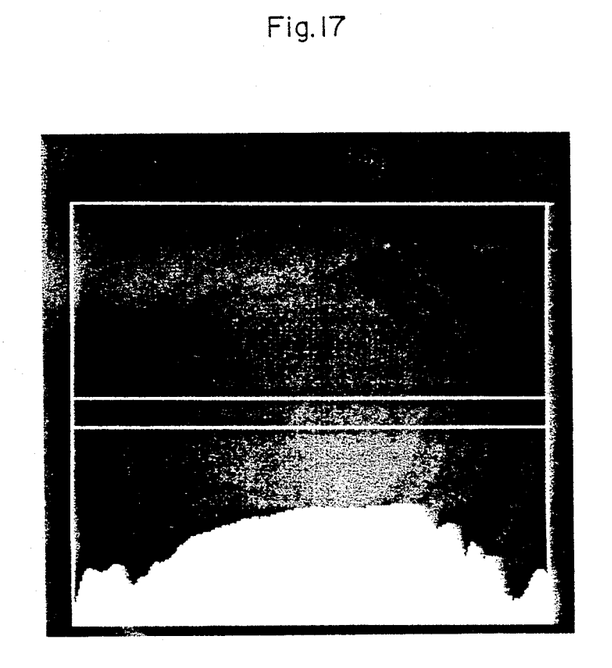
FIG. 17 is a photographic representation similar to FIG. 7 but obtained in a prior art inspection method.

Turning back to FIG. 1 the camera 40 is positioned upwardly of the container 1 in axial alignment with a vertical center axis of the container 1 and the source 20 of the diffused illumination to monitor through an optical lens or lenses 41 light energy transmitted through the container 1. The camera 40 is a solid-state camera comprising an array of CCDs providing 256×256 pixels for monitoring an image of the container bottom. As shown in FIGS. 4 and 5, the source 20 of the diffused illumination in accordance with the first embodiment comprises a lamp source 21 of xenon flash tube, a reflector 22, and a pair of first and second diffuser plates 23 and 24 of differing diffusing surface areas. As shown in FIG. 4, the lamp source 21 and the reflector 22 are received in a bottom barrel 25 within the base 11, while the diffuser plates 23 and 24 are received in an upper barrel 26 mounted on the base 11. The reflector 22 reflects the light from the lamp source 21 to redirect parallel rays of light upwardly toward the diffuser plates 23 and 24. The first and second diffuser plates 23 and 24 are vertically spaced with the first one 23 positioned closer to the container bottom. The first diffuser plate 23 has a diffusing surface of greater areas than the container bottom to direct the diffused illumination over the entire container bottom, while the second diffuser plate 24 has a diffusing surface of smaller areas than that of the first diffuser plate 23. It is noted at this point that the second diffuser plate 24 has its peripheral portion made transparent to direct the light towards the first diffuser plate 23 without substantial attenuation. Thus, as schematically shown in FIG. 5, the first diffuser plate 23 receives at its central portion the diffused light once diffused through the second diffuser plate 24 while receiving at its peripheral portion a nondiffused light directed from the lamp source 21 so that it produces the diffused illumination which is less attenuated at a peripheral portion than at a central portion of the first diffuser plate 23. With this result, the diffused illumination of varying intensity is directed to the bottom of the container 1 to illuminate the peripheral region of the container bottom at a greater intensity than at a central region. Accordingly, the camera 40 perceives the light energy transmitted through the container 1, as seen in a photograph of FIG. 7, which illustrates in an upper half a half of the monitored image and in an lower half the light energy distribution selected with respect to one dimension in the field of view along a band indicated by a pair of white lines. The monitored image represents an averaged image of the light energy in which the light energy or intensity of each pixel is calculated as an averaged value between those of the adjacent pixels. As apparent from the photograph, the light energy transmitted through the peripheral region of the container bottom is greater than that transmitted through the central region to provide a pair of peak values spaced along the selected dimension. This is very contrast to the image as shown in the like photograph of FIG. 17 which is obtained in the conventional system using a source of diffused illumination directing the diffused illumination of equal intensity to the container bottom and in which the there is seen no characteristic change in the monitored light intensity for indication of the boundary of the container bottom.

The second diffuser plate 24 is vertically movable within the upper barrel 26 so to adjust the area of the attenuated illumination at the central portion of the first diffuser plate 23 or that of the container bottom. The upper opening of the upper barrel 25 is sealed by a transparent glass plate 28 on which the first diffuser plate 23 is placed. A screen 29 with a center opening is placed over the first diffuser plate 23 to effectively delimit the illumination toward the container bottom.

Figure 6:
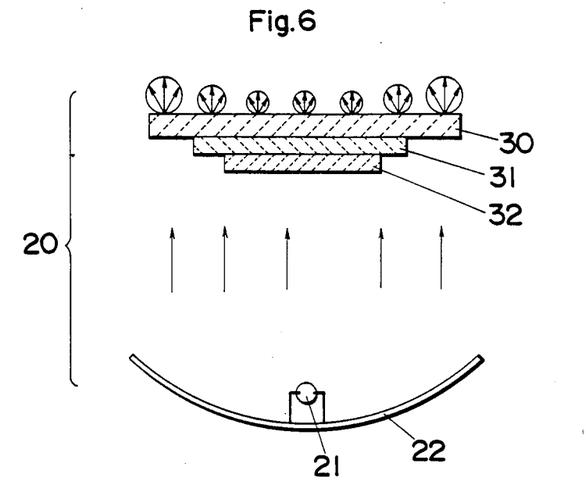
FIG. 6 is a schematic illustration of an alternative diffuser arrangement applicable to the first embodiment.

As an alternative scheme for providing the like diffused illumination of differing intensity, a plurality of diffuser plates 30, 31, and 32 having differing diffusing areas may be stacked in a manner as shown in FIG. 6.

Figure 7:
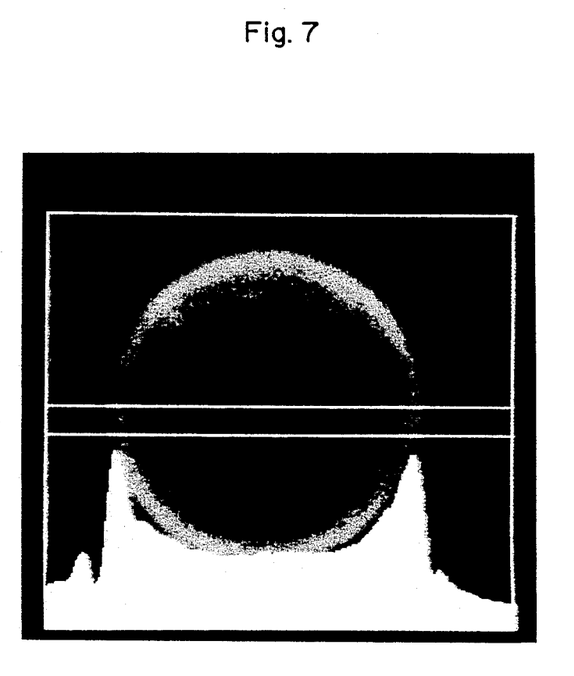
FIG. 7 is a photographic representation illustrating in the upper half a half of monitored image of the container bottom and illustrating in the lower half the monitored light energy distribution selected along a band between a pair of horizontal while lines shown in the figure.

An sequence of detecting a defect on the container bottom based upon the monitored image thereof will be discussed with reference to FIGS. 1 and 7. The analog output signal from the camera 40 is converted at an analog/digital converter 51 to a corresponding digital signal and stored in a frame memory 52. At a bottom shape recognizing section 53 there is determined a true center of the image which corresponds exactly to the center of the container bottom. That is, a pair of lines are firstly selected which are assumed to extend through or nearby the center of the image with the lines being crossed to each other. Then, a light energy distribution like that shown in the lower half of FIG. 7 is obtained with respect to each line. As previously discussed, such light energy distribution indicates clearly a pair of peak values at spaced positions respectively corresponding to the opposed peripheral edges of the container bottom due to the differing illumination level of the peripheral region from the central region of the container bottom. It is therefore easily decided a midpoint between such spaced positions having the peak values with respect to each line. Thereafter, the true center is determined as an intersection of perpendicular bisectors each passing through the midpoint of each line. Based upon thus determined true center of the image, a zone defining section 54 operates to define an inspection zone with a known parameter such as a radius of the container under inspection, which zone is therefore in an exact registration with the container bottom and cover the whole area of the container bottom while excluding a superfluous outside environment. It is within the confines of this defined zone that the defect detection is carried at a defect analysis section 55 with reference to the monitored image stored in the frame memory. Such detection is made by a conventional scanning technique to examine the difference between the magnitude of the signals from the adjacent pixels and recognize a defect when the difference exceeds a predetermined reference.

Upon detection of a defect, a reject section 56 responds to actuate the suction rod 15 of the inspection station 10 to hold the defected container 1 until it is carried by the starwheel 13 to the reject exit 19 for discharging the container 1 to a reject chute.

Figure 8:
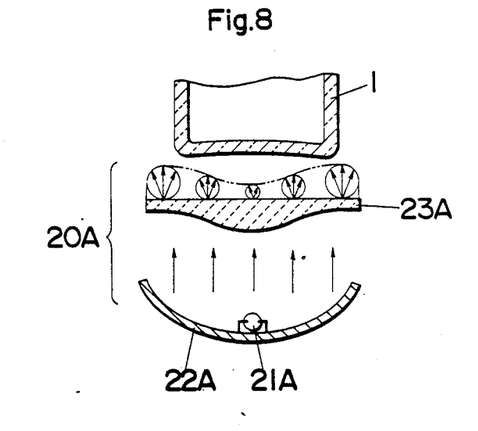
FIGS. 8 to 12 are respectively schematic illustrations of various sources of diffused illumination employed in second to sixth embodiments of the present invention.

Second embodiment <FIGS. 8>

FIG. 8 illustrates another source 20A of diffused illumination which provides the like diffused illumination of directing a more amount of illumination to the peripheral region than to the central region of the container bottom. The source 20A comprises a like lamp source 21A, reflector 22A, and a diffuser plate 23A which is thicker toward its center than at the periphery so as to attenuate the light by absorption to a greater extent at the central portion, thereby providing the intended diffused illumination of varying intensity.

Figure 9:
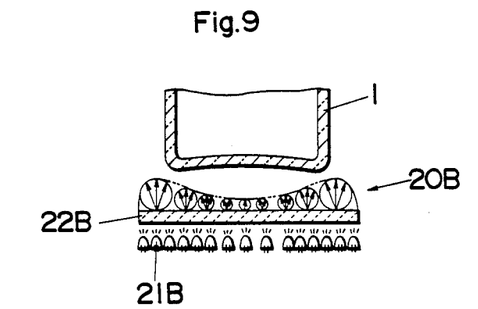

Third embodiment [FIG. 9]

In the third embodiment, a source of diffused illumination 20B utilizes a plurality of minute lamp sources 21B made of light emitting diode [LED] and a single diffuser plate 23B positioned between the lamp sources 21B and the bottom of the container 1. The LEDs 21B are distributed in a plane substantially parallel to the diffuser plate 23B and the container bottom in such a way as to have a greater distribution density toward the periphery than at the center, thereby providing the like diffused illumination of differing intensity.

Figure 10:
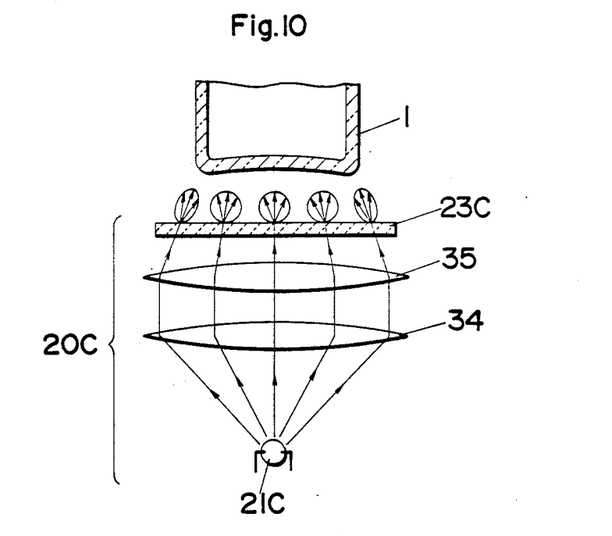

Fourth embodiment <FIG. 10>

A source 20C of diffused illumination in this embodiment utilizes a pair of first and second convergent lenses 34 and 35 between a lamp source 21C and a diffuser plate 23C. The first lens 34 collects the light from the lamp source 21C to provide parallel rays which are then converged by the second lens 35 to provide convergent rays of light which are directed toward the camera through the diffuser plate 23C and the container bottom. With this arrangement, the diffuser plate 23C receives in its peripheral portion a denser rays of light directed to the camera than at the central portion, thereby producing a rather directional diffused illumination for providing a greater illumination level at the peripheral region than at the central region of the container bottom.

Figure 11:
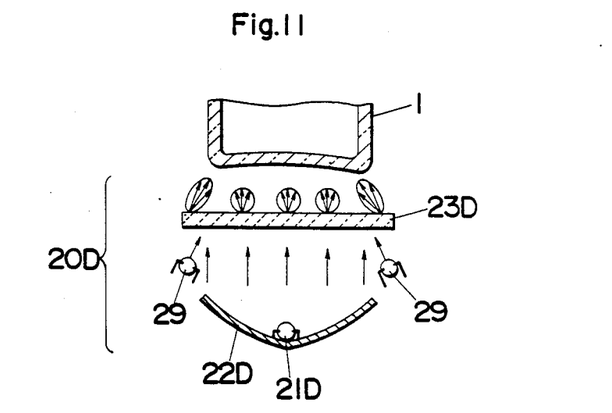

Fifth embodiment <FIG. 11>

A source 20D of diffused illumination in this embodiment utilizes, in addition to a lamp source 21D, a reflector 22D and a diffuser plate 23D, an auxiliary lamp source 29. The auxiliary lamp source 29 includes a plurality of lamps which are arranged around the periphery of the diffuser plate 23D in a closer relation thereto than the lamp source 21D to intensify the diffused illumination toward the peripheral region of the container bottom.

Figure 12:
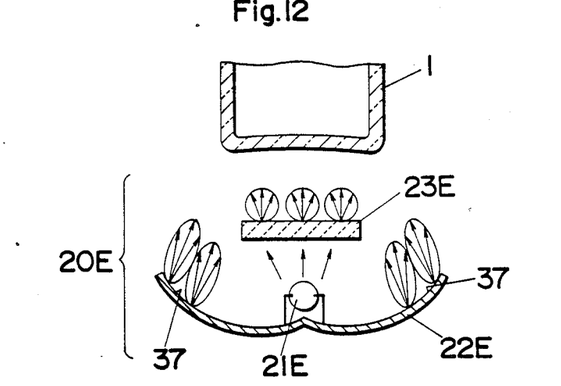

Sixth embodiment <FIG. 12>

In this embodiment, a source 20E comprises a lamp source 21E, a reflector 22E, and a diffuser plate 23E. The diffuser plate 23E is positioned and dimensioned to direct the diffused illumination mainly toward the central portion of the container bottom. The reflector 22E is formed at least in its peripheral portion with a diffusing surface 37 which reflects the light from the lamp source 20E as being diffused thereat and directs the resulting diffused illumination toward the container bottom without passing through the diffuser plate 23D. Thus, the diffused illumination obtained from the reflector 22E and reaching the peripheral portion of the container bottom is free from absorption by the diffuser plate 23E, to thereby illuminate the peripheral region of the container bottom at a greater intensity than at the central region. The central portion of the reflector 22E reflecting the light to the diffuser plate 23E may or may not be finished to produce the diffused illumination.

Figure 13:
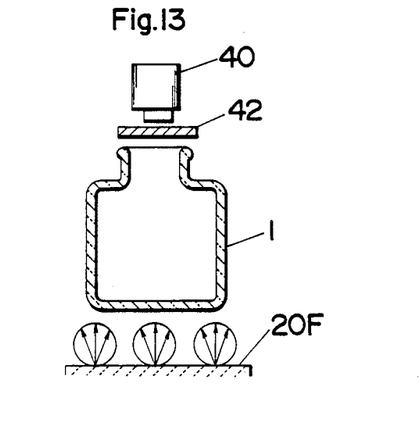
FIG. 13 is a schematic illustration of a transparent container inspection apparatus in accordance with a seventh embodiment of the present invention.

Seventh embodiment <FIG. 13>

Figure 14:
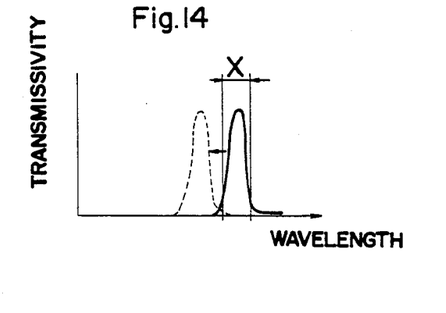
FIG. 14 is a diagram showing a wavelength shifting characteristic to an interference filter employed in the seventh embodiment.

Referring to FIG. 13, a seventh embodiment of the present invention is shown to utilize an interference filter 42 for positively excluding the light energy transmitted through the region other than the container bottom. A source of diffused illumination may be any of those disclosed in the previous embodiment and is schematically shown in FIG. 13 to have a diffusing surface 20F. The interference filter 42 is positioned adjacent the camera 40 and is selected to have a pass band of wavelength corresponding to the light or illumination once transmitted through and thereby colored by the container 1, thus excluding an environmental illumination from entering the camera 40. It is known that the interference filter 42 shows a considerably shifting of the pass band when the angle of incidence becomes more than a critical value, i.e., ±20°, as shown in FIG. 14, and therefore the interference filter 42 will pass the light of particular wavelength selected only when the light reaches the filter at an angle of incidence not exceeding the critical value. That is, as shown in FIG. 14, when the pass band X is selected, the interference filter 42 shows a maximum transmissivity only for the light having the wavelength within the pass band and reaching the filter at an angle of incidence less than the critical angle, and substantially zero transmissivity for light having an angle of incidence exceeding the critical value due to the shifting of the bass band, as indicated by dotted lines in the figure. By better utilization of the above characteristic to the interference filter, the present invention can successfully exclude the light transmitted through the side wall as having a greater angle of incidence with respect to the interference filter 42 than the light transmitted through the container bottom. In view of this, the filter 42 is properly positioned in relation to the container bottom such that the light transmitted only through the container bottom can be passed through the filter for monitoring by camera 40. With this arrangement, there could expect an improved signal-to-noise (S/N) ratio in the image processing, which further enhances the above inspection zone definition and the defect analysis. In the above discussion, the container 1 under inspection is assumed to be a colored container so as to provide the colored light which, after being transmitted through the container, can be discriminated from the other light not transmitted through the same for selective recognition by the camera 40 through the interference filter. However, the same technique can be equally possible for inspection of non-colored containers by providing a color finish on the reflector of the source, diffuser plate, or employing a lamp source producing a light of intended wavelength, or by adding a colore filter for example between a lamp source and a diffuser plate.

What is claimed is:

1. A method of inspecting a transparent container having a defect on the container bottom, said method comprising the steps of:
    directing a source of diffused illumination through the bottom of the container, with said diffused illumination being greater in intensity at a peripheral region of the container bottom than at a central region of the container bottom;
    monitoring light energy transmitted through the container bottom to provide a distribution pattern of said light energy along at least one dimension corresponding to a line extending in the plane of the container bottom;
    obtaining from said light energy distribution pattern a pair of peak values spaced along said dimension and a corresponding pair of positions having said peak values, respectively,
    calculating a true center of the container bottom based upon thus obtained positions and defining based upon said true center an inspection zone in an exact coincidence with the container bottom; and
    analyzing said light energy transmitted through the container bottom within said inspection zone to detect a defect on the container bottom.

2. The method as set forth in claim 1, wherein said true center of the container bottom is determined through the following steps of:
    providing first and second energy distribution patterns respectively along first and second dimensions which corresponds to two reference lines extending in the plane of the container bottom and crossing to each other,
    obtaining a pair of peak values from each of said first and second light energy distribution patterns,
    determining first and second centers respectively on said first and second dimension, and
    obtaining said true center as an intersection of perpendiculars bisectors passing through the first and second centers respectively of said first and second dimensions.

3. The method as set forth in claim 1, wherein said source of diffused illumination is arranged to have a diffusing surface which is substantially in parallel to the plane of the container bottom such that the diffused illumination reaches a sidewall of the container at a smaller angle of incidence than the container bottom to be reflected thereat in the direction outwardly of the container, whereby reducing the light energy to be monitored through the container sidewall in relation to the light energy monitored through the container bottom.

4. The method as set forth in claim 3, wherein said source of diffused illumination comprises a lamp source and a pair of first and second diffuser plates being arranged between the lamp source and the container bottom, the first diffuser plate being positioned and dimensioned to cover the entire container bottom, while the second diffuser plate being positioned and dimensioned to have less diffusing surface area than that of said first diffuser plate such that the light directed toward the central region of the container bottom is twice diffused or attenuated through said first and second diffuser plates while the light directed toward the peripheral region is only once diffused or attenuated through said first diffuser plate, whereby illuminating the peripheral region of the container bottom to a greater intensity than the central region.

5. The method as set forth in claim 4, wherein said second diffuser plate is movable relative to said first diffuser plate in a direction of varying the distance therebetween.

6. The method as set forth in claim 3, wherein said source of diffused illumination utilizes a diffuser plate having a thickness which is greater at a central portion than at a peripheral portion so as to direct said diffused illumination through the container bottom with said diffused illumination being greater in intensity at a peripheral region of the container bottom than at a central region of the container bottom.

7. The method as set forth in claim 3, wherein said source of diffused illumination comprises a plurality of lamp sources and a diffuser plate disposed between said lamps and the container bottom, said lamp sources being arranged to have a distribution density for directing the illumination in greater intensity toward the peripheral region of the container bottom than toward the central region of the container bottom through said diffuser plate.

8. The method as set forth in claim 3, wherein said source of diffused illumination comprises a lamp source, convergent lens means, and a diffuser plate, said convergent lens means converging the rays of light from the lamp source through the diffuser plate to develop a additional amount of the diffused illumination which is oriented through the peripheral region of the container bottom toward a monitoring spot than that is oriented directed through the central region of the container bottom toward said monitoring spot.

9. The method as set forth in claim 3, wherein said source of diffused illumination comprises a first lamp source being disposed in coincidence with the center of the container bottom, a second lamp source being disposed in adjacent relation to the periphery of the container bottom, and a diffuser plate for directing diffused illumination from first and second lamps through the container bottom, said second lamp source being arranged closer to the container bottom than said first lamp.

10. The method as set forth in claim 3, wherein said source of diffused illumination comprises a lamp source, a reflector, and a diffuser plate through which the light from the lamp source passes to provide the diffused illumination directed through the central region of the container bottom, said reflector having a diffuser surface reflecting the light from the lamp source in such a way as to direct the resulting diffused illumination directly toward the peripheral portion of the container bottom without passing through said diffuser plate.

11. The method as set forth in claim 1, wherein said diffused illumination being transmitted through the container bottom is directed through an interference filter toward a camera being provided for monitoring said light energy, said interference filter being selected to have a pass band of wavelength which passes the light transmitted through the container and substantially exclude the entry of a light not transmitted through the container, said interference filter attenuating the light transmitted through the container and arriving at the camera at an incidence angle of more than a preselected value for reducing the light energy transmitted through other than the container bottom.

12. An apparatus for inspecting a transparent container having a defect on the container bottom comprising:
   means for locating the container at an inspection station;
   a source of diffused illumination for directing the diffused light through the bottom of the container located at said inspection station, said diffused illumination being greater in intensity at a peripheral region of the container bottom than at a central region of the container bottom;
   light receiving means including a camera monitoring light energy transmitted through the container bottom and providing a distribution pattern of said monitored light energy along at least one dimension corresponding to a line extending in the plane of the container bottom;
   means for obtaining from said light energy distribution pattern a pair of peak values spaced along said dimension and a corresponding pair of positions having said peak values, respectively;
   calculator means for calculating a true center of the container bottom based upon thus obtained positions and defining based upon said true center an inspection zone in an exact coincidence with the container bottom;
   detector means for analyzing said light energy transmitted through the container bottom within the confines of said inspection zone to detect a defect on the container bottom; and
   reject means for rejecting a container having such detected defect.

13. The apparatus as set forth in claim 12, wherein said source of diffused illumination comprises a lamp source and a pair of first and second diffuser plates being arranged between the lamp source and the container bottom, the first diffuser plate being positioned and dimensioned to cover the entire container bottom, while the second diffuser plate being positioned and dimensioned to have less diffusing surface area than that of the first diffuser plate such that the light directed toward the central region of the container bottom is twice diffused or attenuated through the first and second diffuser plates while the light directed toward the peripheral region is only once diffused or attenuated through said first diffuser plate, whereby illuminating the peripheral region at a greater intensity than the central region of the container bottom.

14. The apparatus as set forth in claim 13, wherein said second diffuser plate is movable relative to said first diffuser plate in a direction of varying the distance therebetween.

15. The apparatus as set forth in claim 12, wherein said source of diffused illumination comprises a lamp source and a diffuser plate being disposed substantially in parallel with the container bottom, said diffuser plate having a thickness which is greater toward a center than at a peripheral portion so as to direct said diffused illumination through the container bottom with said diffused illumination being greater in intensity at a peripheral region than at a central region of the container bottom.

16. The apparatus as set forth in claim 12, wherein said source of diffused illumination comprises a plurality of lamp sources being arranged in a plane substantially in parallel with the container bottom, and a diffuser plate being disposed between said lamp sources and the container bottom, said lamps being arranged to have a greater distribution density at a central portion corresponding to the container bottom central region that at a peripheral portion.

17. The apparatus as set forth in claim 12, wherein said source of diffused illumination comprises a lamp source, convergent lens means, and a diffuser plate, said convergent lens means converging the rays of light from the lamp source through the diffuser plate to develop a additional amount of the diffused illumination which is oriented through the peripheral region of the container bottom toward said detector means than that oriented and directed through the central region of the container bottom toward said detector means.

18. The apparatus as set forth in claim 12, wherein said source of diffused illumination comprises a first lamp source being disposed in coincidence with the center of the container bottom, a plurality of second lamp sources being disposed in adjacent relation to the periphery of the container bottom, and a diffuser plate for directing diffused illumination from first and second lamp sources through the container bottom, said second lamp sources being arranged to be closer to the container bottom than said first lamp source.

19. The apparatus as set forth in claim 12, wherein said source of diffused illumination comprises a lamp source, a reflector, and a diffuser plate through which the light from the lamp source passes to provide the diffused illumination directed through the central region of the container bottom, said reflector having a diffuser surface reflecting the light from the lamp source in such a way as to direct the resulting diffused illumination directly toward the peripheral region of the container bottom without passing through said diffuser plate.

20. The apparatus as set forth in claim 12, including an interference filter positioned adjacent said detector means to direct said light energy transmitted through the container to said detector means, said interference filter being selected to have a pass band of wavelength for passing the light transmitted through the container and for substantially excluding the entry of light not transmitted through the container, said interference filter attenuating the light transmitted through the container and arriving at the detector means at an incidence angle of more than a preselected value for reducing the light energy being transmitted through other than the container bottom.

* * * * *